United States Patent [19]

Habu et al.

[11] 4,088,495

[45] May 9, 1978

[54] SILVER HALIDE PHOTOGRAPHIC ELEMENT CONTAINING A GELATINOUS LAYER HARDENED WITH AN ALIPHATIC HYDROCARBON HAVING AT LEAST THREE VINYLSULFONYL GROUPS

[75] Inventors: Teiji Habu; Shinobu Korematsu; Tsuneo Wada; Takayosi Omura; Hiroki Ishii; Takashi Sasaki, all of Hino, Japan

[73] Assignee: Konishiroku Photo Industry Co., Ltd., Hino, Japan

[21] Appl. No.: 832,067

[22] Filed: Sep. 9, 1977

Related U.S. Application Data

[63] Continuation of Ser. No. 622,396, Oct. 14, 1975, abandoned.

[30] Foreign Application Priority Data

Oct. 14, 1974   Japan ................................ 49-118457

[51] Int. Cl.$^2$ .............................................. G03C 1/30
[52] U.S. Cl. ..................................... 96/111; 260/117; 106/125
[58] Field of Search ......................... 96/111; 260/117; 106/125

[56] References Cited

U.S. PATENT DOCUMENTS

| 2,994,611 | 8/1961 | Heyna et al. | 96/111 |
| 3,490,911 | 1/1970 | Burness et al. | 96/111 |
| 3,689,274 | 9/1972 | Sobel et al. | 96/111 |
| 3,841,872 | 10/1974 | Burness et al. | 96/111 |

Primary Examiner—Won H. Louie, Jr.
Attorney, Agent, or Firm—Haseltine, Lake & Waters

[57] ABSTRACT

A photographic element comprising a support and a gelatin-containing layer coated thereon which contains gelatin having been hardened with a compound having in the molecular structure an aliphatic hydrocarbon chain to which at least 3 vinyl sulfonyl groups are bonded.

5 Claims, No Drawings

SILVER HALIDE PHOTOGRAPHIC ELEMENT CONTAINING A GELATINOUS LAYER HARDENED WITH AN ALIPHATIC HYDROCARBON HAVING AT LEAST THREE VINYLSULFONYL GROUPS

This is a continuation of application Ser. No. 622,396 filed Oct. 14, 1975 now abandoned.

This invention relates to a process for hardening photographic gelatin by use of a novel hardener, and particularly to a gelatin-hardening process suitable for hardening any gelatin-containing layer of a light-sensitive silver halide photographic material.

Generally, light-sensitive silver halide photographic materials are prepared by forming on a proper support, such as glass, paper or synthetic resin film, various layers such as silver halide photographic emulsion layer, filter layer, inter layer, protective layer, sub layer, backing layer, anti-halation layer, etc., which can be called generically as photographic layer. These photographic layers consist of so-called gelatin films composed mainly of gelatin. Accordingly, the physical properties of the photographic layers consisting of gelatin films depend chiefly on those of gelatin. However, gelatin itself has such properties as being low in melting point, high in water swellability and low in mechanical strength. These properties are extremely undesirable as the physical properties of layers of light-sensitive silver-halide photographic materials. It has therefore been an ordinary practice hitherto that various hardeners are reacted with gelatin to crosslink the hardeners with amino, carboxyl, amide and the like functional groups in the gelatin molecules, thereby improving the physical properties of gelatin. As such hardeners, there have been known from old times inorganic hardeners comprising polyvalent metal salts such as chromium alum, chromium trichloride and the like chromium salts or aluminum salts, and organic hardeners such as formalin, glyoxal and acrolein and their derivatives. Photographically, however, these hardeners have various drawbacks, and most of them bring about many such disadvantages as, for example, they are strong in desensitizing action, promote the formation of fog, are too slow in hardening action to be put into practical use, disturb the color forming ability of couplers used in color emulsions, and are excessively rapid in hardening action to make the preparation of light-sensitive photographic materials difficult or, conversely, cannot display desired hardening effects unless incubated sufficiently.

In order to meet quick processing of light-sensitive silver halide photographic materials which has been required recently, not only photographic materials themselves have been improved so as to be in conformity to quick processing, but also processing solutions have been improved so as to be suitable for treatment of such photographic materials. For example, in order to make quick penetration of processing solutions possible, photographic materials have been increased in amount of silver halide and decreased in amount of gelatin so as to be made thinner. Consequently, not only the photographic materials are increased in fog but also the film properties thereof are further deteriorated. Furthermore, with recent propagation of automatic processing machines, photographic materials are required to have film properties sufficiently high in mechanical strength so as to withstand severe mechanical abrasion. In addition, with the spread of high temperature-quick processing by use of strong processing solutions, photographic materials are required to have strong film properties which do not injure the photographic properties. Particularly, in the case of color films, not only the color development itself requires a longer time than in the case of black-and-white development, but also a bleaching treatment is required, in general. Further, in the case of reversal color treatment, the first development should necessarily be effected, so that photographic materials are required to be strong in film hardness.

Accordingly, most of the conventional hardeners bring about disadvantages with progress of quick processing of light-sensitive photographic materials. For example, if only the amount of hardener is increased in order to obtain stronger physical properties of the gelatin film, not only the hardener causes increased desensitization and fogging but also the covering power is lowered. Even if the hardness of film is increased, the film becomes so brittle that the photographic material is difficulty subjected to an automatic processing machine.

An object of the present invention is to provide a hardener which brings about no such disadvantages as mentioned above.

Another object of the invention is to provide a process suitable for hardening photographic gelatin, particularly gelatin films of light-sensitive silver halide photographic materials, by use of the above-mentioned hardener.

Still another object of the present invention is to provide a photographic element which comprises a support and a gelatin-containing layer coated thereon, the physical properties of which layer are improved without deteriorating the photographic properties of the photographic element. Such photographic elements include those having been subjected and not having been subjected to photographic treatment.

These objects can be accomplished by using as the hardener a compound having in the molecular structure thereof an aliphatic hydrocarbon group to which at least three vinylsulfonyl groups have been bonded (hereinafter, the said compound will be referred to as the compound of the present invention).

To use the above-mentioned compound as the hardener, referred to herein, means to react the said compound with gelatin in a stratiform gelatin which is a constitutive layer of light-sensitive photographic material. The said reaction may be carried out according to any of a process in which the compound is added to a coating liquid, which is then coated on a support and dried; a process in which the compound is previously reacted with gelatin, and the reaction product is added to a coating liquid, which is then coated on a support and dried; a process in which a coating liquid containing the compound is coated on a previously formed layer to form a layer, which is then dried; or a process in which a photographic material consisting of a support and photographic layers formed thereon is dipped in a solution of the compound either before or during the development of the photographic material.

Typical examples of the compounds of the present inventon are shown below, but compounds usable in the present invention are not limited to these. Among the below-mentioned compounds those of the acid or base type can be used as salts thereof, and compounds in the form of such salts are also involved in the compounds of the present invention. Examples of the compounds are given below:

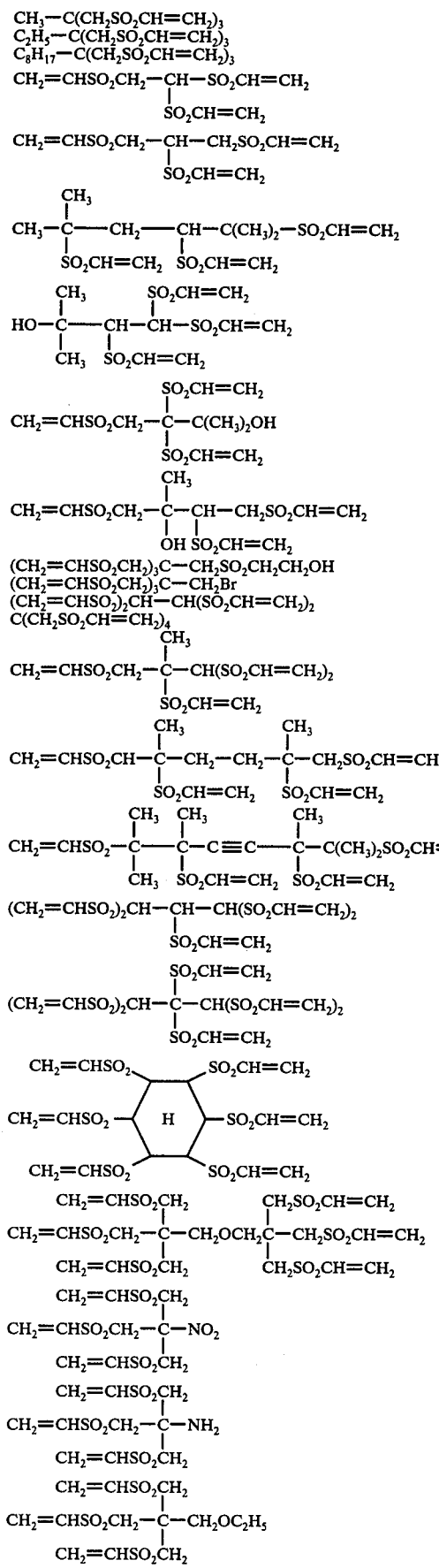

-continued

24. 
$$CH_2=CHSO_2CH_2-\overset{CH_2=CHSO_2CH_2}{\underset{CH_2=CHSO_2CH_2}{C}}-NHCH_2COOH$$

25. 
$$CH_2=CHSO_2CH_2-\overset{CH_2=CHSO_2CH_2}{\underset{CH_2=CHSO_2CH_2}{C}}-NHCH_2CH_2SO_3H$$

Typical procedures for synthesizing the compounds of the present invention are explained below with reference to synthesis examples, but these are not limitative. All the parts are expressed by weight.

SYNTHESIS EXAMPLE 1

(Synthesis of the exemplified compound 2)

To 300 parts of ethanol were successively added 6.9 parts of metallic sodium, 23.4 parts of 2-mercaptoethanol and 18.9 parts of 1,1,1-tris(chloromethyl)propane in this order, and the resulting mixture was heated under reflux. Thereafter, the deposited sodium chloride was removed, and the solution was concentrated to obtain 1,1,1-tris(2-hydroxyethyl-thiomethyl) propane. This compound was added to 50 parts of chloroform, and 45 parts of thionyl chloride was dropped into the resulting mixture. Subsequently, the mixture was heated under reflux, and then the solvent chloroform and unreacted thionyl chloride were removed by distillation under reduced pressure. The residual oily substance was poured into ice water and extracted with ether, and the ether extract was dehydrated over anhydrous sodium sulfate and then freed from the solvent by distillation to obtain 1,1,1-tris(2-chloroethylthiomethyl)propane. To this compound were successively added 0.3 part of phosphoric acid and 60 parts of 30% aqueous hydrogen peroxide, and the resulting medium mixture was heated under reflux and then cooled to deposit 1,1,1-tris(2-chloroethylsulfonylmethyl)propane. The deposited compound was recovered by filtration and dissolved in 200 parts of acetone, and the resulting acetone solution was incorporated with 30 parts of triethylamine and then stirred at room temperature to deposit triethylamine hydrochloride. This hydrochloride was removed, and the acetone solution was concentrated to deposit white solids. The solids were recrystallized from ethanol-acetone to obtain 1,1,1-tris(vinylsulfonylmethyl)propane.

Elementary analysis for $C_{12}H_{20}O_6S_3$:

|  | C | H | S |
|---|---|---|---|
| Calculated (%) | 40.43 | 5.65 | 26.99 |
| Found (%) | 40.29 | 5.55 | 27.03 |

SYNTHESIS EXAMPLE 2

(Synthesis of the exemplified compound 5)

To 300 parts of ethanol were successively added 6.9 parts of metallic sodium, 23.4 parts of 2-mercaptoethanol and 14.7 parts of 1,2,3-trichloropropane in this order, and the resulting mixture was heated under reflux. Thereafter, the deposited sodium chloride was removed, and the solution was concentrated to obtain 1,2,3-tris(2-hydroxyethylthio)propane. This compound was added to 80 parts of chloroform, and 45 parts of thionyl chloride was dropped into the resulting mixture.

Subsequently, the mixture was heated under reflux, and then the solvent chloroform and unreacted thionyl chloride were removed by distillation under reduced pressure. The residual oily substance was poured into ice water and extracted with ether, and the ether extract was dehydrated over anhydrous sodium sulfate and then freed from the solvent by distillation to obtain 1,2,3-tris(2-chloroethylthio)propane. To this compound were successively added 0.3 part of phosphoric acid and 60 parts of 30% aqueous hydrogen peroxide, and the resulting mixture was heated under reflux and then cooled to deposit 1,2,3-tris(2-chloroethylsulfonyl)propane. The deposited compound was recovered by filtration and dissolved in 100 parts of dimethyl sulfoxide, and the resulting solution was incorporated with 30 parts of triethylamine and then stirred at room temperature to deposit triethylamine hydrochloride. This hydrochloride was removed, and then the dimethyl sulfoxide was removed by distillation to deposit solids. The deposited solids were recrystallized from ethanol to obtain 1,2,3-tris(vinylsulfonyl)propane.

Elementary analysis for $C_9H_{19}O_6S_3$:

|  | C | H | S |
|---|---|---|---|
| Calculated (%) | 33.84 | 5.99 | 30.12 |
| Found (%) | 33.65 | 5.89 | 30.31 |

SYNTHESIS EXAMPLE 3

(Synthesis of the exemplified compound 13)

To 400 parts of ethanol were successively added 9.2 parts of metallic sodium, 31.2 parts of 2-mercaptoethanol amd 38.8 parts of pentaerythritol tetrabromide, and the resulting mixture was heated under reflux. Thereafter, the deposited sodium bromide was removed, and the ethanol was removed by distillation to obtain tetrakis(2-hydroxyethylthiomethyl)methane. This compound was added to 80 parts of chloroform, and 60 parts of thionyl chloride was dropped into the resulting mixture. Subsequently, the mixture was heated under reflux, and then the solvent chloroform and unreacted thionyl chloride were removed by distillation under reduced pressure. The residual oily substance was poured into ice water and extracted with ether, and the ether extract was dehydrated over anhydrous sodium sulfate and then freed from the ether by distillation to obtain tetrakis(2-chloroethylthiomethyl)methane. To this compound were successively added 0.4 part of phosphoric acid and 80 parts of 30% aqueous hydrogen peroxide, and the resulting mixture was heated under reflux and then cooled to deposit tetrakis(2-chloroethylsulfonylmethyl)methane. The deposited compound was recovered by filtration and dissolved in 200 parts of acetone, and the resulting solution was incorporated with 40 parts of triethylamine and then stirred at room temperature to deposit triethylamine hydrochloride. This hydrochloride was removed, and the acetone was removed by distillation to deposit solids. The deposited solids were recrystallized from acetone-ethanol to obtain tetrakis(vinylsulfonylmethyl)methane.

Elementary analysis for $C_{13}H_{20}O_8S_4$:

|  | C | H | S |
|---|---|---|---|
| Calculated (%) | 36.10 | 4.66 | 29.65 |
| Found (%) | 36.02 | 4.52 | 29.81 |

In incorporating the thus synthesized compound of the present invention as hardener into photographic layers of a light-sensitive silver halide photographic material, the compound may be formed into a solution in one or more of water and common organic solvents such as methanol, ethanol, acetone, methyl ethyl ketone, ethyl cellosolve, methyl cellosolve, acetonitrile, dioxane, dimethylformamide, dimethyl sulfoxide, ethyl acetate, halogenated alcohol, chloroform, etc., and then added to a coating liquid for forming eqch of said layers. It is also possible to overcoat the said hardener solution on the uppermost layer of said layers.

The amount of the compound of the present invention to be added to the coating liquid for forming gelatin film varies depending on the kind, physical properties, photographic properties, etc., of the objective gelatin film, but is ordinarily from 0.01 to 100% by weight, preferably from 0.1 to 10% by weight, based on the dry weight of gelatin in the coating liquid. The compound may be added at any stage during preparation of the coating liquid. To a silver halide emulsion for example, however, the compound is preferably added after second ripening of the emulsion.

Light sensitive silver halide photographic materials, to which the present invention is applicable, include all such light-sensitive photographic materials as, for example, black-and-white, color and pseudocolor photographic materials, and ordinary, printing, X-raysensitive and radiation-sensitive photographic materials which may be any of negative, positive, direct-positive and the like types.

Silver halide emulsions used in the abovementioned light-sensitive silver halide photographic materials may contain as sensitive components all kinds of silver halides such as silver chloride, silver iodide, silver bromide, silver iodobromide, silver chlorobromide, silver chloroiodobromide, etc. Further, these emulsions may be subjected to various types of chemical sensitization such as noble metal sensitization using salts of noble metals such as ruthenium, rhodium, palladium, iridium, gold, etc., e.g. ammonium chloropalladate, potassium chloroplatinate, potassium chloropalladite, potassium chloroaurate, etc., sulfur sensitization using sulfur compounds, selenium sensitization using selenium compounds, reduction sensitization using stannous salts, polyamides, etc., and sensitization using polyalkylene oxide type compounds, or to optical sensitization using cyanine, merocyanine and the like dyes. Further, the emulsions may be incorporated with couplers, stabilizers, e.g. mercury, triazole, azaindene, benzothiazolium and zinc compounds, wetting agents, e.g. dihydroxylkanes, antistatic agents, film modifiers comprising water-dispersible, fine granular polymeric substances obtained by emulsion polymerization, coating aids, e.g. saponin and polyethylene glycol lauryl ether, and the like various photographic additives.

In the present invention, the compound of the present invention may, if necessary, be used in combination with other hardeners.

As supports for light-sensitive silver halide photographic materials to which the hardening process of the present invention is applied, there may be used, for example, paper, laminated paper, glass, and films and sheets of cellulose acetate, cellulose nitrate, polyester, polyamide, polystyrene, etc. These are properly selected according to the intended use of the photographic materials.

When applied to gelatin films of a light-sensitive silver halide photographic material, the compound of the present invention displays an effective hardening ability without deteriorating such photographic properties as fog and speed of the photographic emulsion. Further, the compound of the present invention scarcely causes post-hardening due to incubation to make it possible to obtain a light-sensitive photographic material stabilized in quality. Even when the light-sensitive photographic material is stored over a long period of time, the compound of the present invention not only makes the photographic material more stable without any detrimental effect on the photographic emulsions but also shows such excellent hardening action as to sufficiently withstand high temperature quick processing and automatic processing.

Characteristics of the hardening process of the present invention are well displayed particularly when techniques of high level are required, like in the case of color photographic materials. As mentioned previously, in color development adopted in the processing of color photographic materials, there is required a longer period of time than in the case of black-and-white development. Further, color photographic materials are ordinarily subjected to bleaching treatment. Thus, the total time required for the processing of color photographic materials is long. Moreover, for the processing of reversal color photographic materials, the first development is additionally required, and for the processing of external type reversal color photographic materials, the color development operation is repeated several times. Accordingly, color photographic materials suitable for high temperature processing are required to be strong in film hardness. According to the hardening process of the present invention, it is possible to prepare films capable of sufficiently withstanding the above-mentioned processing. Moreover, the compound of the present invention is well stable over a long period of time or against heat attack, and hence makes it possible to prepare color photographic materials which are free from disadvantages derived from excessive hardening and are stabilized in quality.

Another characteristic of color photographic materials is that they are complex in composition and contain various compounds. Even when applied to color photographic materials containing couplers, e.g. 5-pyrazolone type magenta couplers, naphthol or phenol type cyan couplers, open-chain ketomethylene type yellow couplers, so-called 2-equivalent or 4-equivalent couplers thereof, or so-called masking couplers having arylazo groups in the active points, the hardening process of the present invention does not cause any uneven color development that is frequently observed when other hardeners are used. Further, the hardening process of the present invention is effectively applicable, if necessary, to color photographic materials containing ultraviolet absorbers, fluorescent brighteners, mordant layers, color developers, of such development inhibitor-yielding type compounds as disclosed in Japanese Patent Laying Open-to-Public No. 77653/1974.

The present invention is illustrated in more detail below with reference to examples, but the modes of practice of the present invention are not limited to the examples, and various modifications are possible within the scope of the invention.

EXAMPLE 1

A neutral silver iodobromide emulsion for a negative containing 1.5 mole% of silver iodide was incorporated with gold and sulfur sensitizers, and subjected to second ripening. After the ripening, the emulsion was further incorporated with 4-hydroxy-6-methyl-1,3,3a,7-tetrazaindene as a stabilizer, diethylene glycol as a wetting agent, and saponin as a coating aid. Thereafter, the emulsion was divided into 6 portions. One of the portions was coated onto a polyester (polyethylene terephthalate) film base and then dried to prepare a control sample. The remaining 5 portions of the emulsion were incorporated individually with a methanol or dimethyl sulfoxide-methanol solution containing each of 1,2-bis(-vinylsulfonyl)ethane and the exemplified compounds (2), (4), (13) and (17). The amount of each compound was $10^{-4}$ mole per gram of gelatin contained in the emulsion. The portions thus treated were individually coated onto a polyester film base and then dried to prepare samples.

The control samples and 5 kinds of samples were measured for their respective hardening characteristics according to the below-mentioned procedure. That is, each of these samples after coating and drying was stored for 1 day at 25° C. and 55% RH, stored for 30 days under the same conditions as above, and subjected to heat treatment at 50° C. and 80% RH for 3 days. Each of the samples thus treated was dipped in a 1.5% aqueous sodium hydroxide solution kept at 50° C. to measure the time before the gelatin film began to dissolve. Separately, each of the samples, which had been stored and heat-treated under the same conditions as above, was dipped for 2 minutes in a 3% aqueous sodium carbonate monohydrate solution at 25° C. Immediately thereafter, the surface of the gelatin film was wiped off, and then scratched with a sapphire needle having a tip of 1 mm. in radius to measure a load applied to the needle at the time when scratches began to form on the film surface. The value of the load thus measured was taken as a film surface strength of each sample.

Further, the samples after coating and drying were individually stored at 25° C. and 55% RH for 1 day, and then subjected to sensitometry to measure the speed and fog of each sample.

The results obtained in the above measurements were as shown in Table 1, in which the speed of each sample was represented by a relative value when that of the control sample was taken as 100.

Table 1

| | Hardening characteristics | | | | | | | |
|---|---|---|---|---|---|---|---|---|
| | Time required for initiation of dissolution (min.) | | | Film surface strength (g) | | | Photographic properties | |
| Compound | Stored for 1 day | Stored for 30 days | Heat-treated for 3 days | Stored for 1 day | Stored for 30 days | Heat-treated for 3 days | Speed | Fog |
| Control sample | 0.5 | 1.0 | 1.0 | 4 | 7 | 15 | 100 | 0.15 |

Table 1-continued

| | Hardening characteristics | | | | | | | |
|---|---|---|---|---|---|---|---|---|
| | Time required for initiation of dissolution (min.) | | | Film surface strength (g) | | | Photographic properties | |
| Compound | Stored for 1 day | Stored for 30 days | Heat-treated for 3 days | Stored for 1 day | Stored for 30 days | Heat-treated for 3 days | Speed | Fog |
| 1,2-Bis(vinyl-sulfonyl)ethane | 2 | 3.5 | 5 more than | 120 | 190 | 280 | 93 | 0.13 |
| Exemplified compound (2) | 16 | 18 | 20 | 200 | 235 | 310 | 88 | 0.12 |
| Exemplified compound (4) | 11 | 15 more than | 20 more than | 205 | 290 | 350 | 90 | 0.12 |
| Exemplified compound (13) | 15 more than | 20 more than | 20 more than | 180 | 220 | 250 | 93 | 0.13 |
| Exemplified compound (17) | 20 | 20 | 20 | 145 | 160 | 200 | 96 | 0.14 |

As is clear from Table 1, the compounds of the present invention are more excellent in resistance to alkali solutions than such a conventional hardener as 1,2-bis(-vinylsulfonyl)ethane, are less in post-hardening due to storage under ambient conditions and to heat treatment, and display markedly excellent hardening activity without deteriorating the photographic properties.

Example 2

A film assembly having the below-mentioned layers on a cellulose acetate film base was prepared and was used as a control sample containing no hardener.

First layer — Anti-halation layer
Second layer — Red-sensitive silver halide emulsion layer containing a cyan coupler
Third layer — Gelatin inter layer
Fourth layer — Green-sensitive silver halide gelatin emulsion layer containing a magenta coupler and the development inhibitor-yielding type compound disclosed in Japanese Patent Laying Open-to-Public No. 77635/1974
Fifth layer — Filter layer containing yellow colloidal silver
Sixth layer — Blue-sensitive silver halide gelatin emulsion layer containing a yellow coupler
Seventh layer — Gelatin protective layer Separately, samples were prepared in such a manner that each of bis(vinylsulfonylmethyl)ether as a control compound and the exemplified compounds (5) and (12) of the present invention was incorporated into each of the above-mentioned layers in a proportion of $0.5 \times 10^{-4}$ mole per gram of gelatin contained in each layer.

The hardening characteristics of each sample were measured in the same manner as in Example 1. Further, the photographic properties of each sample were measured in such a manner that the sample was exposed through a wedge to white light, color developed at 38° C. for 3 minutes by use of a color developer containing 4-amino-3-methyl-N-ethyl hydroxyethylaniline sulfate as a developing agent, and subjected to ordinary bleaching, fixing and water-washing, and then to sensitometry. The results obtained were as set forth in Table 2, in which the speed of each sample was represented by a relative value when that of the control sample was taken as 100, and B, G and R show that sensitometry was effected by measuring the color density of each sample through blue, green and red filters, respectively.

Table 2

| | Hardening characteristics | | | | | | | | | | | |
|---|---|---|---|---|---|---|---|---|---|---|---|---|
| | Time required for initiation of dissolution (min.) | | | Film surface strength (g) | | | Photographic properties | | | | | |
| | Stored for 1 day | Stored for 30 days | Heat-treated for 3 days | Stored for 1 day | Stored for 30 days | Heat-treated for 3 days | Speed | | | Fog | | |
| Compound | | | | | | | B | G | R | B | G | R |
| Control sample | 1 | 2 | 5 more than | 10 | 16 | 25 | 100 | 100 | 100 | 0.10 | 0.10 | 0.15 |
| Bis(vinyl-sulfonyl-methyl)ether | 10 | 18 | 20 | 200 | 310 | 380 | 92 | 90 | 85 | 0.08 | 0.08 | 0.12 |
| Exemplified compound (5) | more than 20 | more than 20 | more than 20 | 330 | 400 | 410 | 96 | 93 | 90 | 0.08 | 0.08 | 0.12 |
| Exemplified compound (12) | 15 | more than 20 | more than 20 | 300 | 320 | 350 | 93 | 89 | 87 | 0.07 | 0.07 | 0.12 |

From Table 2, it is understood that when applied to color photographic films, the compounds of the present invention display excellent hardening action without deteriorating the photographic properties.

Further, each of the above-mentioned samples was subjected also to reversal color processing (first development, water-washing, reversal exposure, second development, water-washing, bleaching, water-washing, fixing and water-washing). As the result, the control sample showed the formation of marked scratches on the film surface, whereas each of the samples according to the present invention maintained excellent film properties and were not particularly deteriorated in photographic properties.

EXAMPLE 3

A silver chlorobromide emulsion containing 30% of silver bromide was incorporated with gold and sulfur sensitizers, and subjected to a second ripening. After the ripening, the emulsion was further incorporated with a stabilizer, a coating aid and a magenta coupler, and then divided into 4 portions. One of the portions was coated onto a polyethylene laminated paper and then dried to prepare a control sample containing no hardener. The remaining 3 portions of the emulsion were incorporated individually with an acetone-methanol solution containing each of the exemplified compound (5) and such control compounds as 1,2-bis(vinylsulfonyl)ethane and 1,3,5-tris(vinylsulfonyl)benzene. The amount of each compound was $10^{-4}$ mole per gram of gelatin contained in the emulsion. The portions thus treated were individually coated onto a polyethylene laminated paper and then dried to prepare 3 kinds of samples containing hardeners.

Each of the thus prepared samples were measured in their respective hardening characteristics in the same manner as in Example 1, and was color developed at 30° C. for 3 minutes and 30 seconds with a color developer containing 3-methyl-N-ethyl-$\beta$-methanesulfonamido-ethyl-4-aminoaniline sulfate as a developing agent, and was subjected to bleach-fixing and water-washing, and then to sensitometry. The results obtained were as set forth in Table 3, in which the speed was represented by a relative value when that of the control sample was taken as 100. The sensitometry was carried out by measuring the reflection density through a green filter.

Table 3

| | Hardening characteristics | | | | | | | |
|---|---|---|---|---|---|---|---|---|
| | Time required for initiation of dissolution (min.) | | | Film surface strength (g) | | | Photographic properties | |
| Compound | Stored for 1 day | Stored for 30 days | Heat-treated for 3 days | Stored for 1 day | Stored for 30 days | Heat-treated for 3 days | Speed | Fog |
| Control sample | 0.5 | 0.5 | 3 | 5 | 5 | 12 | 100 | 0.05 |
| Exemplified compound (5) | 15 | 20 | more than 20 | 70 | 110 | 130 | 97 | 0.04 |
| 1,2-Bis(vinyl-sulfonyl)ethane | 4 | 7 | 8 | 45 | 130 | 150 | 97 | 0.04 |
| 1,3,5-Tris(vinyl-sulfonyl)benzene | 13 | more than 20 | more than 20 | 60 | 80 | 120 | 95 | 0.04 |

From Table 3, it is understood that the compound of the present invention displays markedly excellent hardening action without deteriorating the photographic properties, and is less in post-hardening due to storage under ambient conditions and to heat treatment than in the case of the known similar compounds.

What we claim is:

1. A silver halide photographic element comprising a support and at least one gelatinous layer coated thereon, said layer being hardened with a compound selected from the group consisting of

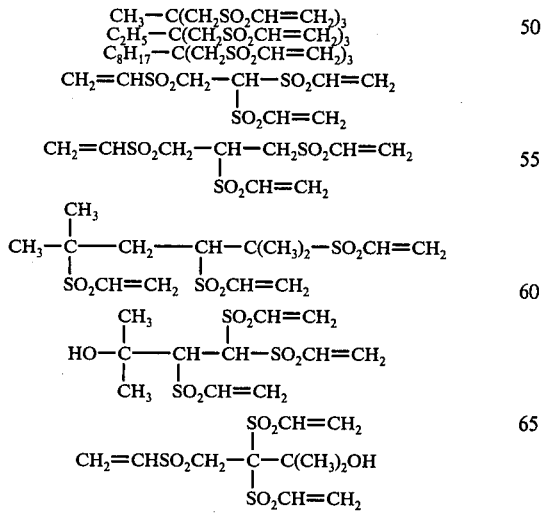

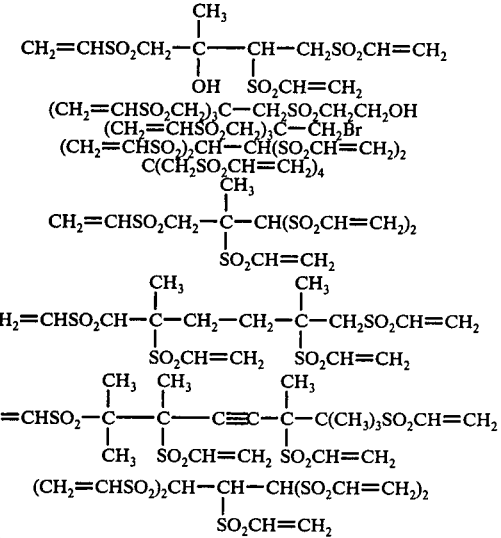

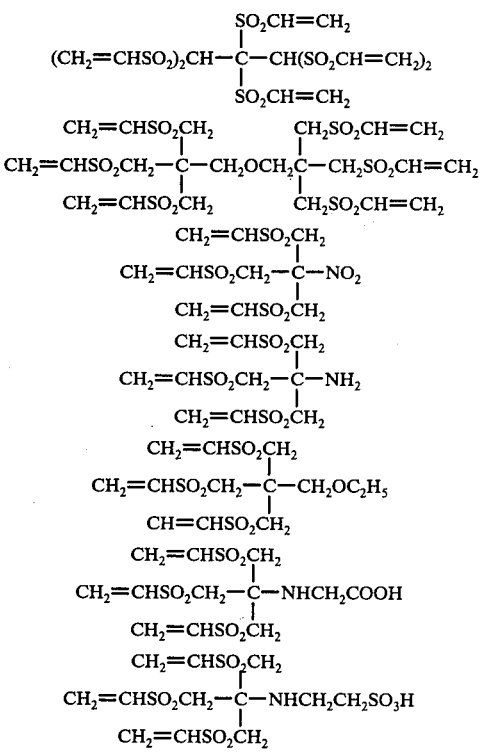

2. A silver halide photographic element comprising a support and at least one gelatinous layer coated thereon, said layer being hardened with a compound selected from the group consisting of

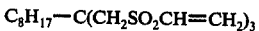

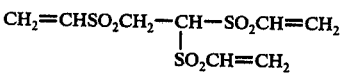

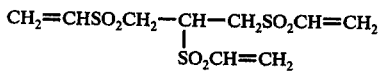

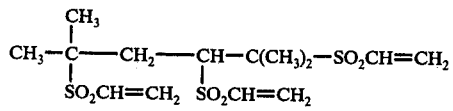

(CH$_2$=CHSO$_2$)$_2$CH—CH(SO$_2$CH=CH$_2$)$_2$

C(CH$_2$SO$_2$CH=CH$_2$)$_4$

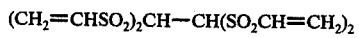

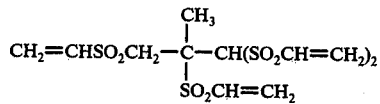

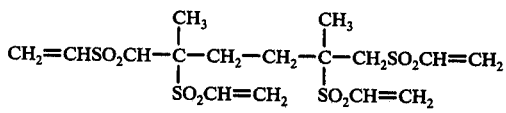

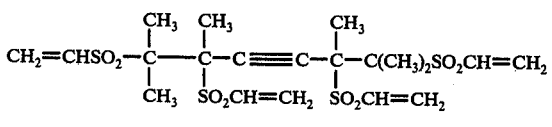

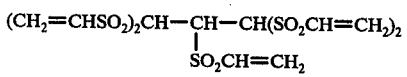

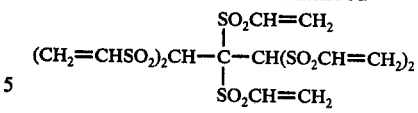

3. A silver halide photographic element comprising a support and at least one gelatinous layer coated thereon, said layer being hardened with a compound having the formula:

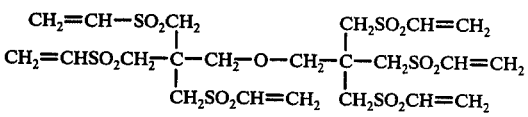

4. A silver halide photograhic element comprising a support and at least one gelatinous layer coated thereon, said layer being hardened with a compound selected from the group consisting of:

C$_2$H$_5$—C(CH$_2$SO$_2$CH=CH$_2$)$_3$ (CH$_2$=CHSO$_2$)$_2$CH—CH(SO$_2$CH—CH$_2$)$_2$

C(CH$_2$SO$_2$CH=CH$_2$)$_4$

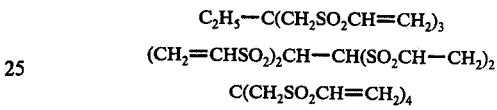

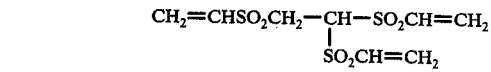

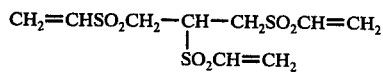

5. A silver halide photographic element comprising a support and at least one gelatinous layer coated thereon, said layer being hardened with a compound selected from the group consisting of a compound having the formula:

C$_2$H$_5$C(CH$_2$SO$_2$CH=CH$_2$)$_3$ and a compound of the formula:

* * * * *